US009827150B1

(12) United States Patent
Sheehan

(10) Patent No.: US 9,827,150 B1
(45) Date of Patent: Nov. 28, 2017

(54) ABSORBENT ARTICLE PACKAGE WITH ENHANCED OPENING AND RECLOSEABILITY

(71) Applicant: The Procter & Gamble Company, Cincinnati, OH (US)

(72) Inventor: Astrid Annette Sheehan, Symmes Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/364,319

(22) Filed: Nov. 30, 2016

(51) Int. Cl.
| *A61F 13/15* | (2006.01) |
| *A61F 13/551* | (2006.01) |
| *B65D 75/58* | (2006.01) |
| *B65D 85/62* | (2006.01) |

(52) U.S. Cl.
CPC .... *A61F 13/5511* (2013.01); *A61F 13/55115* (2013.01); *A61F 13/55145* (2013.01); *B65D 75/5827* (2013.01); *B65D 85/62* (2013.01)

(58) Field of Classification Search
CPC . B65D 75/5827; B65D 85/62; A61F 13/5511; A61F 13/55145; A61F 13/55115; A61F 13/55105
USPC .................. 206/494, 440; 383/207, 208, 200
See application file for complete search history.

(56) References Cited

U.S. PATENT DOCUMENTS

| 3,610,516 A | 10/1971 | Esty |
| 3,929,678 A | 12/1975 | Laughlin et al. |
| 4,259,217 A | 3/1981 | Murphy |
| 5,050,742 A | 9/1991 | Muckenfuhs |
| 5,179,164 A | 1/1993 | Lausberg et al. |
| 5,226,534 A * | 7/1993 | Kim ...................... B65D 71/20 206/349 |
| 5,261,899 A | 11/1993 | Visscher et al. |
| 5,265,783 A * | 11/1993 | Iqbal .................... B65D 33/065 224/610 |
| 5,361,905 A | 11/1994 | McQueeny et al. |
| 5,380,094 A | 1/1995 | Schmidt et al. |
| 5,427,245 A | 6/1995 | Roussel |

(Continued)

FOREIGN PATENT DOCUMENTS

| CA | 2014331 | 5/1991 |
| DE | 9105943 | 7/1991 |

(Continued)

*Primary Examiner* — Steven A. Reynolds
(74) *Attorney, Agent, or Firm* — Andrew J. Hagerty; William E. Gallagher

(57) ABSTRACT

A package containing a stack of folded disposable absorbent articles, the package being formed of flexible polymeric film, and having a path of perforations or scoring defining a serpentine-shape, is disclosed. The serpentine-shaped path may be located proximate the fold noses of the articles in the stack for easy tactile identification, grasping and withdrawal of individual ones thereof, and may be configured so as to cause opening flaps defined by the path to effectively draw to a closed position following access to the contents within, whereby the package may be used to store the unused supply of articles following opening. The package, and printed commercial artwork and product information on the package surfaces, may be configured such that the fold noses are disposed at the apparent bottom of the package, for improved standing stability when the package is shelved.

11 Claims, 18 Drawing Sheets

(56) References Cited

U.S. PATENT DOCUMENTS

| | | | |
|---|---|---|---|
| 5,655,843 A | 8/1997 | Conrad et al. | |
| 6,126,317 A * | 10/2000 | Anderson | B65D 75/5827 229/87.05 |
| 6,258,308 B1 | 7/2001 | Brady et al. | |
| 6,265,512 B1 | 7/2001 | Siedle et al. | |
| 7,370,760 B2 | 5/2008 | Clough | |
| 7,887,660 B2 | 2/2011 | Jeruzal et al. | |
| 7,910,658 B2 | 3/2011 | Chang et al. | |
| 8,114,522 B2 | 2/2012 | Kitora et al. | |
| 8,230,998 B2 | 7/2012 | Boldra et al. | |
| 9,169,366 B2 | 10/2015 | Weisman et al. | |
| 2002/0179626 A1* | 12/2002 | Huang | B65D 83/0805 221/63 |
| 2005/0008010 A1 | 1/2005 | Reed | |
| 2005/0288644 A1* | 12/2005 | Mizutani | A61F 13/505 604/385.02 |
| 2007/0151887 A1* | 7/2007 | Clark, Jr. | B65D 75/46 206/494 |
| 2010/0159167 A1 | 6/2010 | Schumacher | |
| 2010/0310198 A1 | 12/2010 | Port et al. | |
| 2011/0062042 A1 | 3/2011 | Boldra et al. | |
| 2012/0237746 A1 | 9/2012 | O'Donnell et al. | |
| 2013/0220864 A1 | 8/2013 | Von Malortie | |
| 2014/0202907 A1* | 7/2014 | Carlen | A61F 13/55115 206/438 |
| 2014/0348444 A1 | 11/2014 | Puccini | |
| 2014/0348445 A1 | 11/2014 | Siesto Casanova et al. | |
| 2015/0104627 A1 | 4/2015 | O'Donnell et al. | |
| 2015/0343748 A1 | 12/2015 | Broyles et al. | |
| 2016/0068323 A1 | 3/2016 | Suryanarayanan et al. | |
| 2016/0107826 A1* | 4/2016 | Motsch | B65D 85/16 383/120 |

FOREIGN PATENT DOCUMENTS

| | | |
|---|---|---|
| EP | 0 414 549 A2 | 2/1991 |
| EP | 0 425 008 A1 | 5/1991 |
| EP | 2 050 689 A1 | 8/2011 |
| JP | 0582862 U | 11/1993 |
| JP | 2520228 Y2 | 12/1996 |
| JP | 3044120 U | 12/1997 |
| JP | 3044735 U | 1/1998 |
| JP | H 10101097 A | 4/1998 |
| JP | 3045026 B2 | 5/2000 |
| JP | 2001-301859 A | 10/2001 |
| JP | 2003-292043 A | 10/2003 |
| JP | 2004-001802 A | 1/2004 |
| JP | 2007-022636 A | 2/2007 |
| JP | 2008-137712 A | 6/2008 |
| JP | 4220076 B2 | 2/2009 |
| JP | 4428708 B2 | 3/2010 |
| JP | 2010-215265 A | 9/2010 |
| JP | 2011-136741 A | 7/2011 |
| JP | 4721263 B2 | 7/2011 |
| JP | 4807236 B2 | 11/2011 |
| JP | 2013-028401 A1 | 2/2013 |
| JP | 2014-198588 | 10/2014 |
| JP | 5683646 B2 | 3/2015 |
| JP | 2015-107803 A | 6/2015 |
| WO | WO 93-08874 A1 | 5/1993 |
| WO | WO 93-08876 A1 | 5/1993 |
| WO | WO 98-24711 | 6/1998 |
| WO | WO 98-38105 | 9/1998 |
| WO | WO 98-43890 | 10/1998 |
| WO | WO 2011-158265 A1 | 11/2011 |
| WO | WO 2013-035280 A1 | 3/2013 |
| WO | WO 2013-187366 A1 | 12/2013 |
| WO | WO 2014-080878 A1 | 5/2014 |

* cited by examiner

ABSORBENT ARTICLE PACKAGE WITH ENHANCED OPENING AND RECLOSEABILITY

BACKGROUND OF THE INVENTION

Non-fragile, compressible consumer products such as disposable absorbent articles (e.g., diapers and training pants, disposable adult incontinence pants and feminine hygiene pads) are often packaged and sold at retail (i.e., placed on display and for sale in a retail store) in soft packages formed of polymer film. Such packages may be formed from one or more sheets of polymer film, seamed via application of heating energy, which has caused portions of the film to melt and fuse along the seams.

After opening a package of disposable absorbent articles and removing one or more items needed for immediate use, a consumer may wish to leave the remaining unused supply of product in the package for storage until the next time additional items are needed. Thus, it is often desirable that the package retain, to some extent, its shape and structural integrity to remain useful as a container for storing unused product following opening. Additionally, and particularly in environments where substantial quantities of airborne dust and dirt particles may be present, it may be desired that the package not only retain its shape and structural integrity, but have a recloseability capability that allows the package to be reclosed to an extent suitable to help protect the unused product from airborne contaminants.

To date, film package opening features have generally been less than fully satisfactory. Various prior configurations of opening perforations have not provided easy opening features, and in addition or alternatively, tend to promote substantial destruction of the package during opening, rendering it unsatisfactory for use as a storage container. To date, known recloseability features, generally, have not proven to be cost effective for the manufacturer operating in highly competitive markets.

Consequently, there is room for improvement in film package opening features.

DESCRIPTION OF EXAMPLES

Definitions

Figure 1:
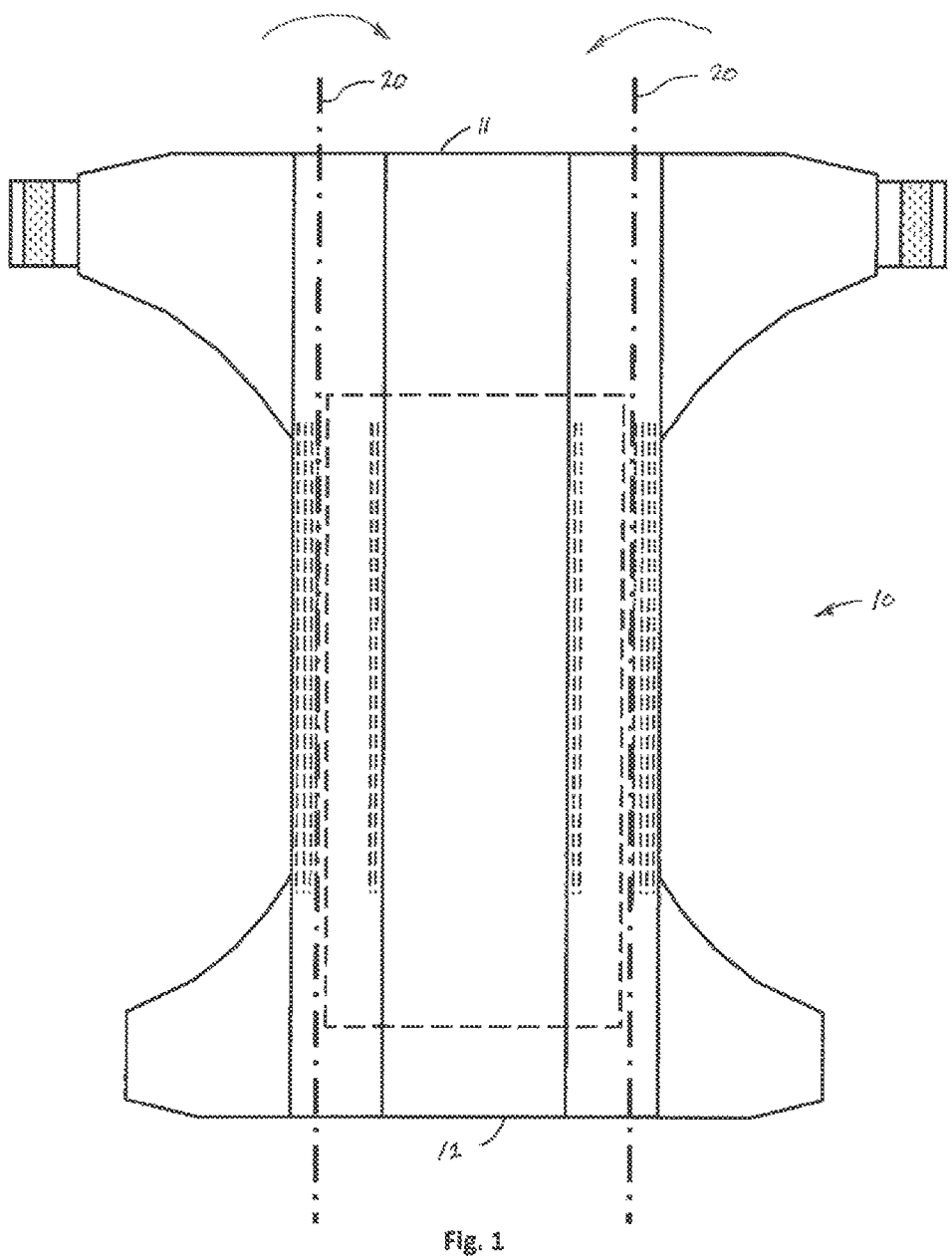
FIG. 1 is a plan view of an example of a disposable absorbent article in the form of a disposable diaper, wearer-facing surfaces facing the viewer.

"Film" means a sheet structure having a length, width and thickness (caliper), wherein each of the length and width greatly exceed the thickness, i.e., by a factor of 1,000 or more, the structure having one layer (monolayer) or more respectively adjacent layers (multilayer), each layer being a substantially continuous structure formed of one or more thermoplastic polymer resins (including blends thereof).

"High Density Polyethylene" (HDPE) means a type of polyethylene defined by a density equal to or greater than 0.941 g/cm$^3$.

"Low Density Polyethylene" (LDPE) means a type of polyethylene defined by a density equal to or less than 0.925 g/cm$^3$.

"Medium Density Polyethylene" (MDPE) means a type of polyethylene defined by a density range of 0.926-0.940 g/cm$^3$.

With respect to a disposable diaper, disposable absorbent pant, or feminine hygiene pad, "lateral" and forms thereof refer to a direction parallel with the waist edges and/or perpendicular to the direction of wearer's standing height when the article is worn.

"Linear Low Density Polyethylene" (LLDPE) means a type of Low Density Polyethylene characterized by substantially linear polyethylene, with significant numbers of short branches, commonly made by copolymerization of ethylene with longer-chain olefins. Linear low-density polyethylene differs structurally from conventional low-density polyethylene (LDPE) because of the absence of long chain branching. The linearity of LLDPE results from the different manufacturing processes of LLDPE and LDPE. In general, LLDPE is produced at lower temperatures and pressures by copolymerization of ethylene and such higher alpha-olefins as butene, hexene, or octene. The copolymerization process produces a LLDPE polymer that has a narrower molecular weight distribution than conventional LDPE and in combination with the linear structure, significantly different rheological properties.

With respect to a disposable diaper, disposable absorbent pant, or feminine hygiene pad, "longitudinal" and forms thereof refer to a direction perpendicular with the waist edges and/or parallel to the direction of the wearer's standing height when the article is worn.

With respect to quantifying the weight fraction or weight percentage of a component of a polymer resin composition forming a film or layer thereof, "predominately" (or a form thereof) means that the component constitutes the largest weight fraction or weight percentage among all components of the composition.

Package; Packaging Film

Referring to FIGS. 1 through 5C, a retail package 49 of non-fragile, compressible disposable absorbent articles 10 (such as, for example, disposable diapers, training pants or adult incontinence pants) may be formed of a polymer film. The film may be a single layer (monolayer), or may have two, three or more layers (multilayer). A multilayer film may have, for example, an outer skin layer formed of a first polymer and an inner skin layer formed of a second polymer. (As used herein, the terms "outer" and "inner" refer to the positioning of the layer relative the inside and the outside of the finished package; thus, the "inner layer" faces the contained product, and the "outer layer" faces outward and has an outer surface that is exposed to view and touch by, e.g., shoppers in a retail store.)

Figure 2:
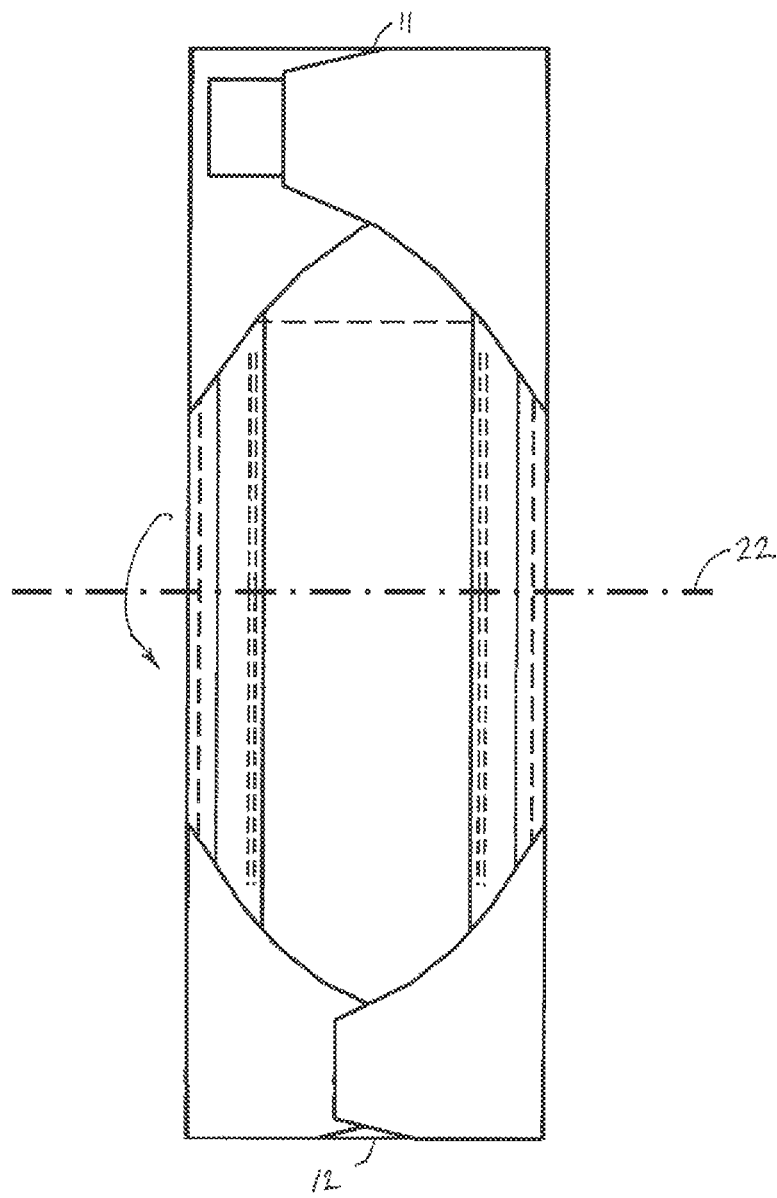
FIG. 2 is a plan view of the diaper of FIG. 1, shown with side portions folded over and laterally inward about longitudinal side edge fold lines.
Figures 3A, 3B:
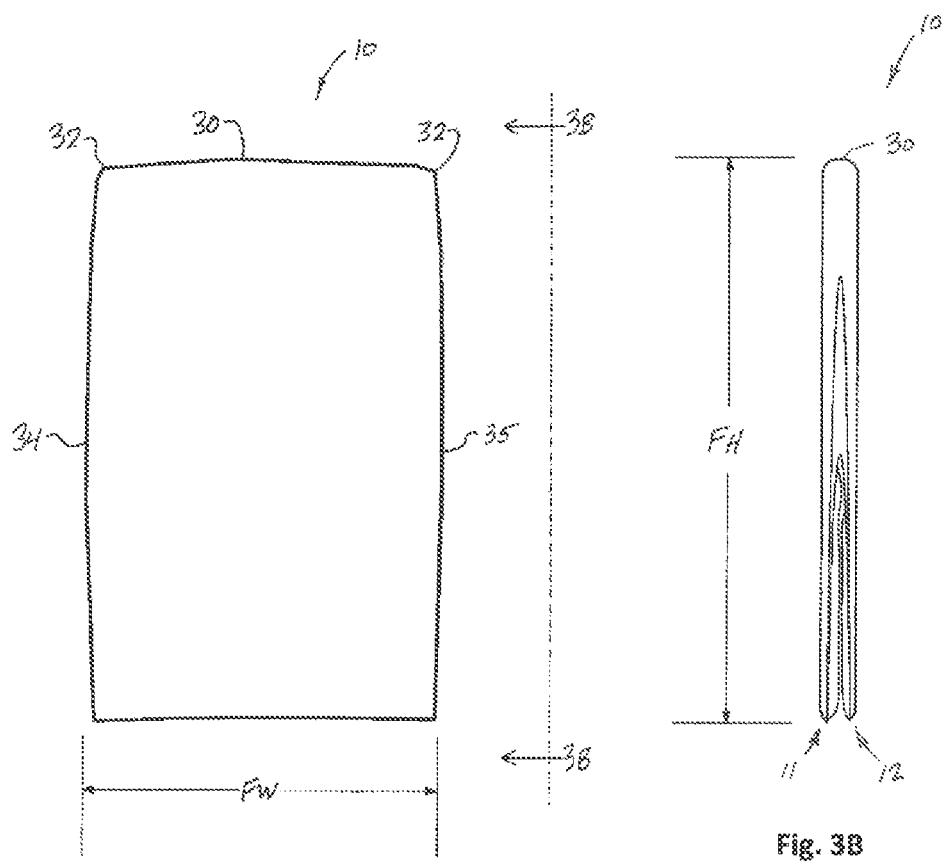
FIG. 3A is a plan view of the diaper of FIG. 2, shown folded about a lateral fold line, wearer-facing surfaces in and outward-facing surfaces out.
FIG. 3B is an edge side view of the folded diaper shown in FIG. 3A.
Figure 4A:
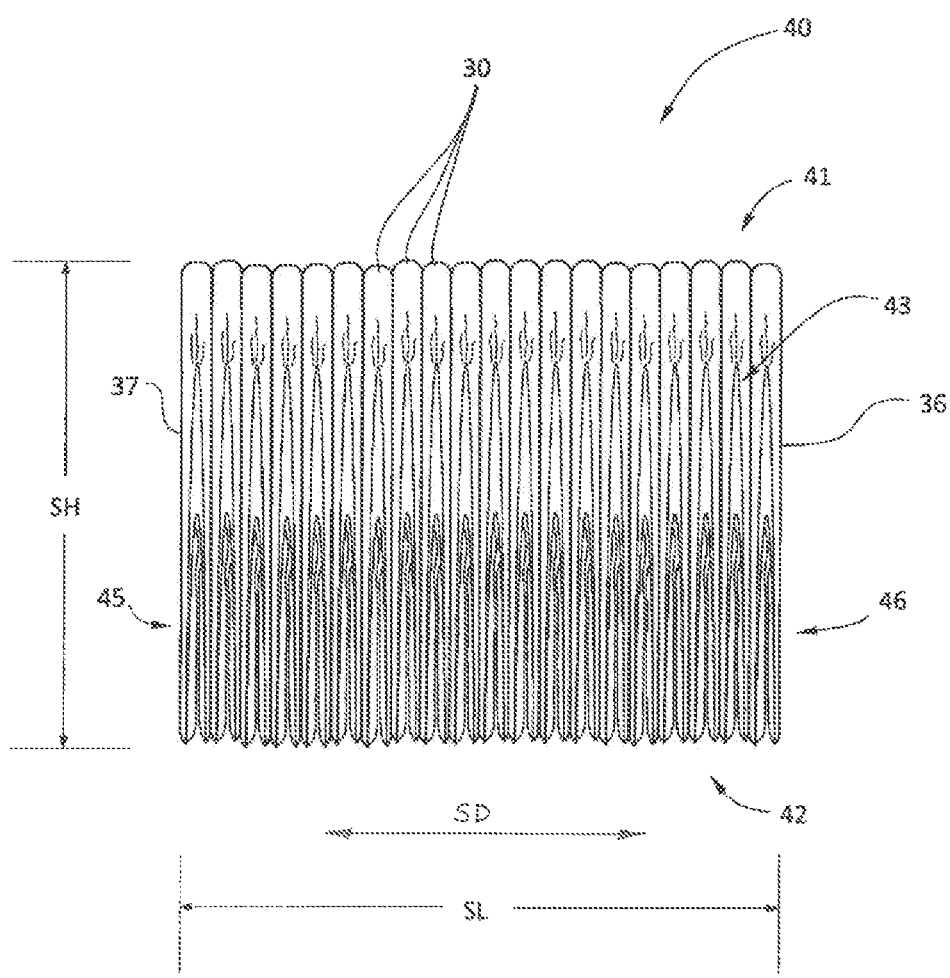
FIG. 4A is an edge side view of a stack of a plurality of folded diapers such as the folded diaper shown in FIGS. 3A and 3B.
Figure 4B:
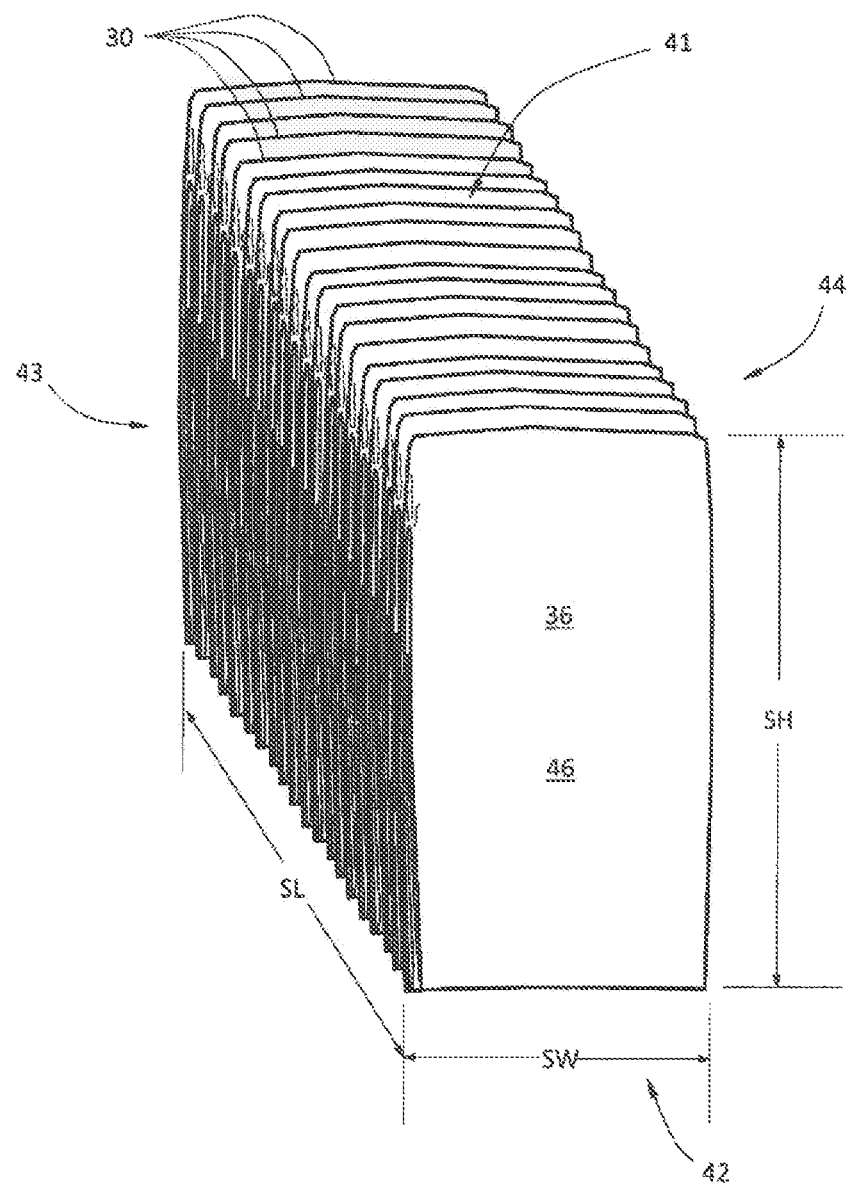
FIG. 4B is a perspective view of the stack of FIG. 4A.

FIGS. 1-3 depict an example of a disposable diaper with front and rear waist edges 11, 12, in successively open/unfolded and folded. FIGS. 4A and 4B depict a stack of a plurality of disposable diapers such that depicted in FIGS. 1-3. For packaging in bulk, each of a plurality of disposable diapers such as that shown in FIG. 1 may, in a possible first step, have its longitudinal side portions be folded over and laterally inward about longitudinal side edge fold lines 20, as may be appreciated from a comparison of FIGS. 1 and 2. Next, the diaper may, in a second step, be folded longitudinally, about lateral fold line 22 that passes through the crotch region of the diaper, as may be appreciated from a comparison of FIGS. 2 and 3. For a bi-fold configuration such as depicted in FIGS. 3A, 3B and 4, the article may be folded longitudinally once, and may in some examples be folded approximately in half about the lateral fold line. For a tri-fold configuration (not shown), the article may be folded longitudinally twice, about two longitudinally-spaced lateral fold lines. In some examples a tri-fold configuration may have the article folded approximately in thirds, about the two longitudinally-spaced lateral fold lines.

Regardless of whether the article is in a bi-fold or tri-fold configuration, the folded article such as folded diaper 10 will have a single fold nose 30 defining at least one end edge of the folded article, fold nose corners 32, and left and right side edges 34, 35. (It will be appreciated that in a tri-fold example, a single fold nose may define each of both end edges of the folded article.) In some examples such as depicted in FIGS. 3A and 3B, fold nose 30 may be proximate the crotch region of the article (the middle region of the article adapted to be located between the wearer's legs during wear). The folded article will have a folded width FW measured as the distance between side edges, and a folded height FH measured as the distance between end edges. A plurality of folded articles such as depicted in FIGS. 3A and 3B may then be placed in similar orientation and neatly stacked together face-to-face to form a stack 40 such as depicted in FIGS. 4A and 4B. In another example (not shown), a first set of the plurality of folded articles may have their fold noses oriented along one side of the stack, and a second set of the plurality of folded articles may be rotated 180 degrees to have their fold noses oriented along the opposite side of the stack. In some examples, the articles in the first set and the articles in the second set may appear in alternating sequence in the stack. For purposes of economy of space in packaging, packing, shipping and shelving, stack 40 may be compressed to a desired degree of compression, along the stack direction SD.

Referring to FIGS. 4A and 4B, stack 40 will have an approximate rectangular cuboid form with a stack height SH approximately corresponding to the folded height FH of the individual folded articles, a stack width SW approximately corresponding to the folded width FW of the individual folded articles, and a stack length SL measured from a first outward-facing side 36 of a first article in the stack to an opposing second outward-facing side 37 of a last article in the stack, along stacking direction SD. Stack 40 may have a first side 41 and an opposing second side 42, one or both of which are defined by approximately aligned fold noses of folded articles in the stack. Stack 40 may have opposing third and fourth sides 43, 44, both of which are defined by approximately aligned side edges 34, 35 of folded articles in the stack. Stack 40 may have opposing fifth and sixth sides 45, 46, each of which is defined by one of first and second outward facing sides 36, 37 of first and last articles at each end of the stack.

Figure 5A:
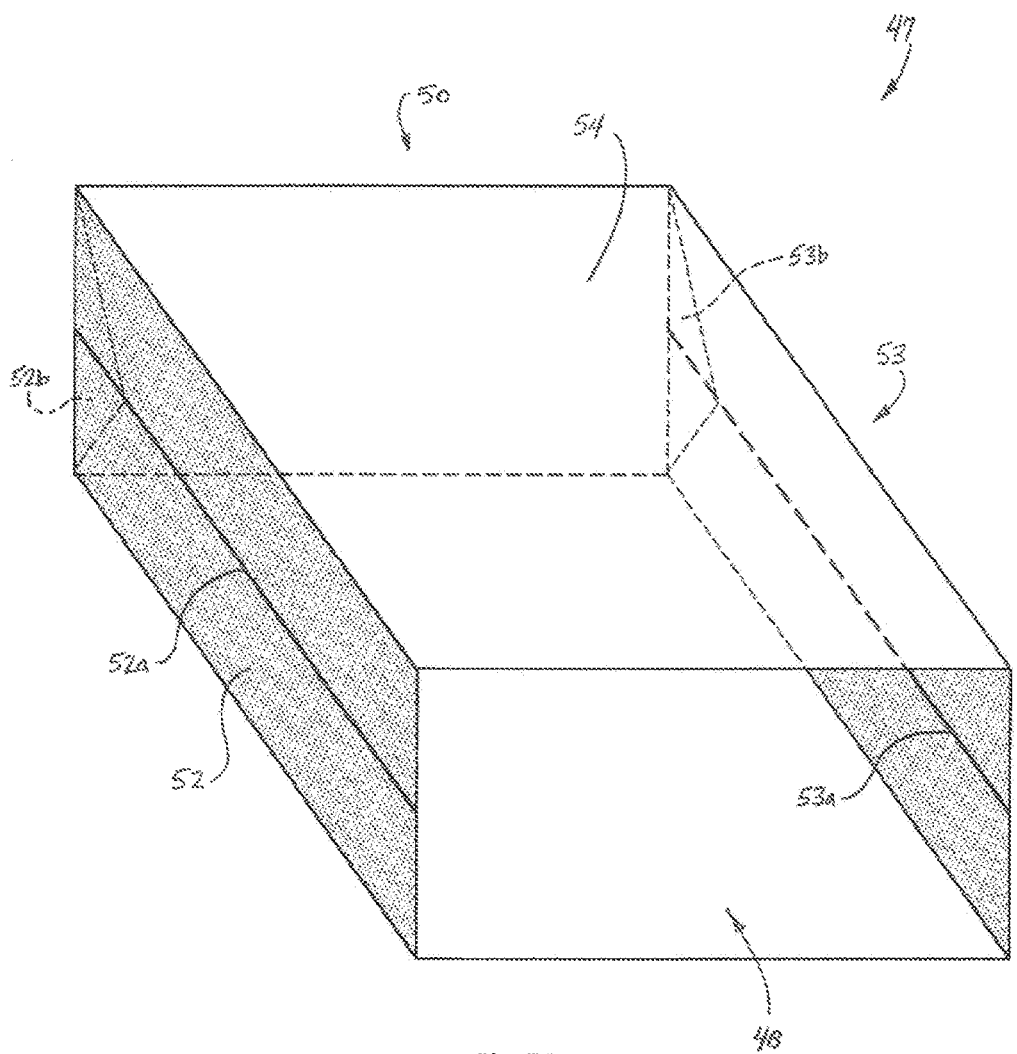
FIG. 5A is a perspective view of a film bag structure from which a film package may be formed.
Figure 5B:
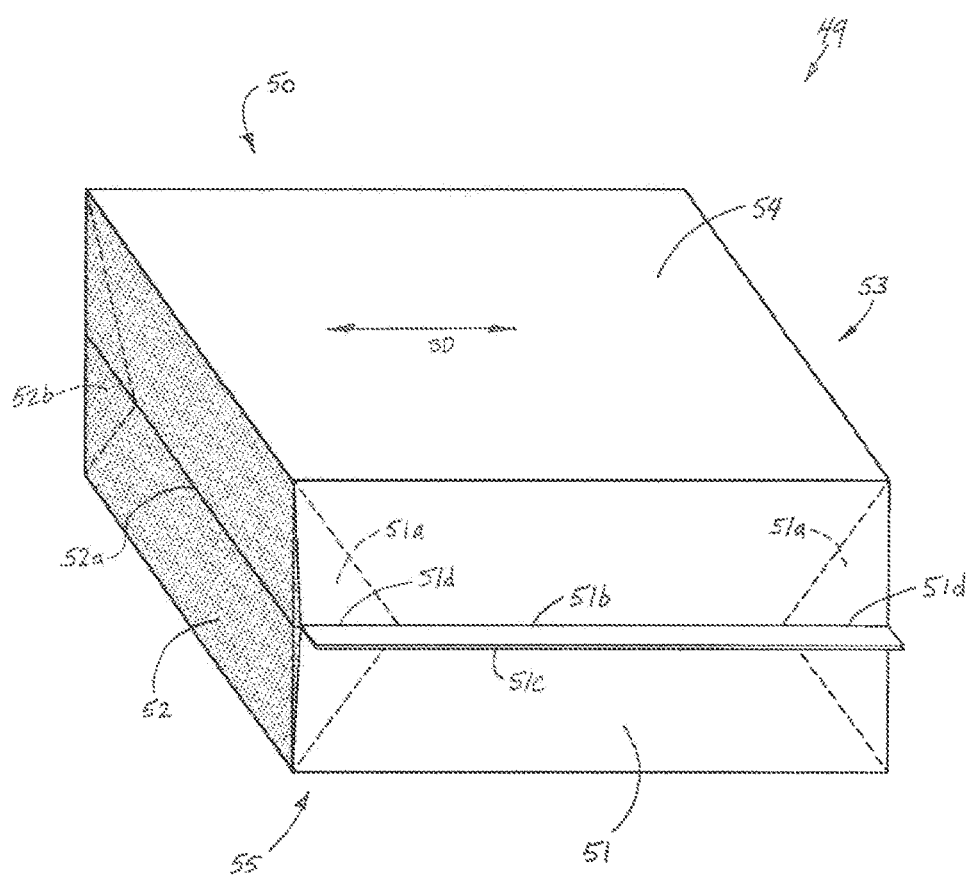
FIG. 5B is a perspective view of a film package that may be used to contain a stack of disposable absorbent articles such as the stack shown in FIG. 4.
Figure 5C:
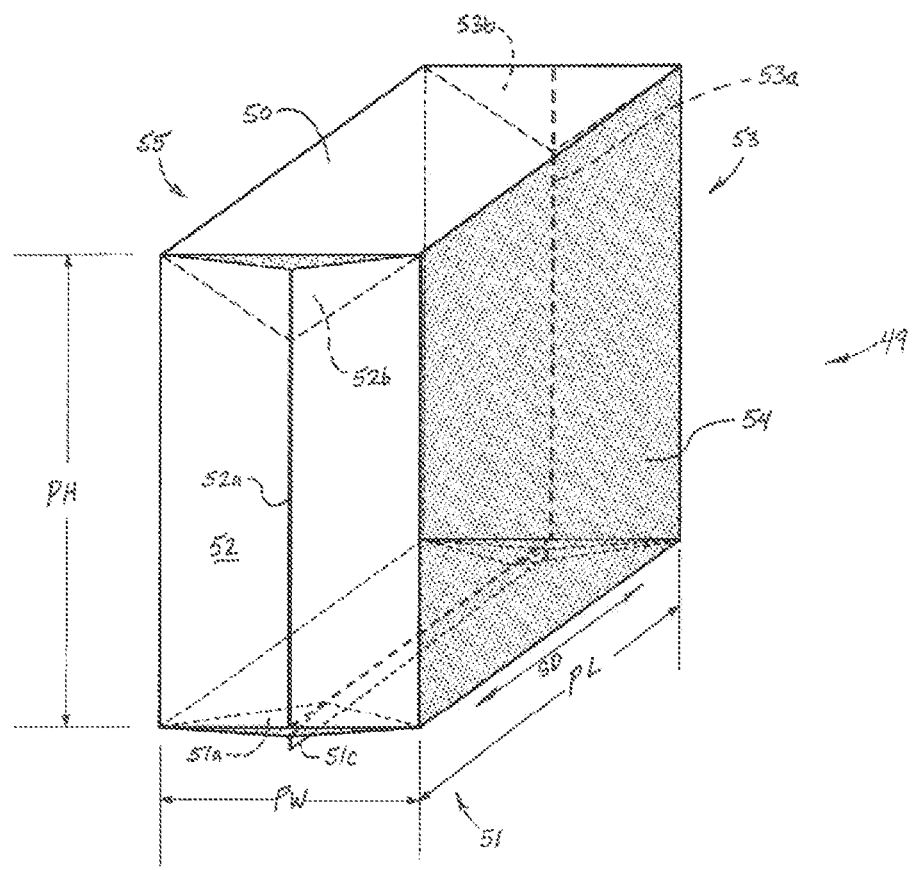
FIG. 5C is an alternative perspective view of the film package shown in FIG. 5B.

Referring to FIG. 5A, a bag structure 47 may be formed from a single sheet of film stock that is suitably folded to form bag gussets 52b, 53b and then joined along portions by bonding to form two side seams 52a, 53a on opposite sides, to form bag structure 47 with no seam on a first package surface 50, and open at the other end 48 (e.g., a gusseted bag structure). Thereafter, the bag structure may be filled by inserting product such as stack 40 of diapers through the open end 48. In a first example, stack 40 of diapers may be inserted first side 41 first, such that after insertion the fold noses inside the package are adjacent first package surface 50. In another example, stack 40 of diapers may be inserted first side 41 last (i.e., second side 42 first), such that after insertion the fold noses inside the package are adjacent second package surface 51. As may be appreciated from FIGS. 5B and 5C, the open end 48 opposite first package surface 50 may then be closed by suitably folding to form closing gussets 51a, bringing the film edges together, and bonding them together to form end seam 51b and second package surface 51. The bag structure 47 and stack 40 dimensions may be suitably selected and effected through design, folding, stacking, compression and packaging processes such the film of the package is taut about the stack at least along the stacking direction SD, to retain the individual diapers 10 in place within the stack 40, maintain stack compression, and maintain a neat, stable, approximate rectangular cuboid shape for the stack 40, and as a result, the package 49. Because the package 49 is formed of flexible polymer film, when suitably sized relative the stack 40 dimensions, package 49 will approximately assume the approximate rectangular cuboid shape and dimensions of the stack 40, when the package film is taut, or otherwise when any loose film is pressed against the stack. When the package film is taut about the stack along directions generally parallel with the stacking direction, in a manner that helps maintain stack compression along the stacking direction, the package will have a package length PL approximately corresponding to the stack length SL, and a package width approximately corresponding to the stack width SW. If the package structure is sized to provide no head space adjacent one or both of first and second sides 41, 42 of packaged stack 40 (i.e., no slack is present in the package film adjacent first and second sides 41, 42 of the stack after the package 49 is formed), the package will have a package height PH approximately corresponding to the stack height SH. In some examples, however, the film package structure may be sized to provide head space, and correspondingly, slack film, adjacent one or both of the first 41 and second 42 sides of stack 40, such as may be desired to provide material for easy grasping about a path of perforations or scoring, for easier tearing.

In the configuration to which reference is made above, the left and right side edges 34, 35 of the folded diapers in the stack 40, and corresponding third and fourth sides 43, 44 of stack 40 will be adjacent fifth and/or sixth package surfaces 54 and 55. It may be desired that the stack size and bag configuration and dimensions be selected such that fifth and sixth package surfaces 54 and 55 are the largest surfaces, or front and rear "faces," of the package. In this arrangement, when the film of the package is taut about the stack, the film of the third, fourth, fifth and sixth package surfaces 52, 53, 54 and 55 is in tension along directions approximately parallel to the approximate plane of the first surface 50, serving to at least partially maintain any compression of the stack 40 along the stacking direction SD.

In some examples, the film stock may be supplied preprinted with desired commercial artwork, graphics, trademark(s) and/or verbal or graphic product information, prior to formation of the bag structure.

The bonds forming any or all of the seams such as seams 52a, 53a and 51b may be created by welding. (Herein, "weld" refers to a union between separate portions of film stock, effected by application of direct or indirect (e.g., ultrasonic) heating energy and pressure that causes separate portions of the film to at least partially melt and fuse together to some extent, forming a bonded area, joint or seam which cannot be separated without substantial destruction to the remainder of one or both joined portions.) If bag-forming and/or packaging machinery forms welds in the film that join the film stock to itself by applying heating energy that causes the film to fuse to itself, it may be desirable that the film stock be multilayer film, and that the layer(s) to be brought into contact and fused be formed of polymer(s) that have lower melting temperature(s) than those of the polymer (s) used to form the other layer(s). This enables heating energy to be applied to a degree sufficient to heat the layer(s) in contact and cause them to fuse, but not sufficient to cause undesired melting and deformation of the other layer(s), which could cause the package to be misshapen and/or displace and/or distort printing on the film stock.

A multilayer film may be co-formed (such as by coextrusion), or in another example, individual layers may be separately formed and then laminated together following their formation, by use of a suitable laminating adhesive. In this latter example, an advantage provided is that one of the layers may be printed on one side before lamination. Following that, the printed side may be faced inward (facing the other layer(s)) during lamination, such that it is protected by the other layer(s) from abrasion and wear in the finished film product, thereby preserving the integrity of the printed images, graphics, verbal content, etc. A suitable multilayer film may be formed of one or more polyolefins, such as polypropylene and polyethylene. In one example, the stock film may have at least two layers, including a first layer of predominately polyethylene and second layer of predominately polypropylene. In one example, a layer formed of predominately polypropylene having a first relatively higher melting temperature, and a layer of predominately polyethylene having a second relatively lower melting temperature, may be used to form the outer and inner layers, respectively. In another example, an inner layer may be formed predominately of a first type of polyethylene having a relatively lower melting temperature, and an outer layer may be formed predominately of a second type of polyethylene having a relatively higher melting temperature.

In an application such as described herein, a multilayer film may be preferred. A multilayer film may have layers of polymer compositions particularly chosen for the characteristics they impart to the film. For example, one or two outer skin layers may be formed of compositions chosen for, e.g., surface gloss; printability; smooth feel; pliability; low noise generation (upon being handled and manipulated, as by a consumer); relatively lower melt temperature and fusibility/ weldability; or any combination of these characteristics. One or more intermediate layers may be formed of compositions chosen for, e.g., tensile strength; stiffness; toughness; suitability for inclusion of blended-in recycled material; environmentally-friendly and/or sustainable material sourceability; relatively higher melt temperature; co-extrusion compatibility with adjacent layers (such that strong bonding between layers occurs upon co-extrusion); or any combination of these characteristics. For film stock in which only one side of the film will be placed in contact with itself and welded, a two-layer film may suffice. For film stock in which both sides of the film will be placed in contact with itself and welded, a film having at least three layers, with two outside skin layers that are weldable, may desired. It will be appreciated that a package having the configuration depicted in FIGS. 5B and 5C requires the film to be welded to itself on both sides—on the generally outer film surface at the gussets 51a, 52b and 53b, and on the generally inner film surface along all other portions of the seams 51b, 52a and 53a.

Film Composition

A multilayer film may include first outside skin layer, second outside skin layer, and intermediate layer disposed between the skin layers.

Each of the layers may include a base polymer. Base polymers may include polyolefins, particularly polyethylenes, polypropylenes, polybutadienes, polypropylene-ethylene interpolymer and copolymers having at least one olefinic constituent, and any mixtures thereof. Certain polyolefins can include linear low density polyethylene (LLDPE), low density polyethylene (LDPE), medium density polyethylene (HDPE), high density polyethylene (HDPE), isotactic polypropylene, random polypropylene copolymers, impact modified polypropylene copolymer, and other polyolefins which are described in PCT Application Nos. WO 99/20664, WO 2006/047374, and WO 2008/086539. Other base polymers such as polyesters, nylons, polyhydroxyalkanoates (or PHAs), copolymers thereof, and combinations of any of the foregoing may also be suitable. In addition, polyolefin plastomers and elastomers could be used to form the multilayer polymeric films. Examples of such suitable polyolefin plastomers and elastomers are described in U.S. Pat. No. 6,258,308; U.S. Publication No. 2010/0159167 A1; and PCT Application Nos. WO 2006/047374 and WO 2006/017518. In one embodiment, such polyolefin plastomers and/or elastomers may comprise up to 25% by volume of the multilayer polymeric film. Other useful polymers include poly-α-olefins such as those described in PCT Application No. WO 99/20664 and the references described therein.

In some examples, one or both of the skin layers may be formed of predominately MDPE, LDPE or LLDPE, more preferably LLDPE. A skin layer formed of predominately LLDPE may be particularly preferred because it imparts the skin layer with a good combination of weldability, relatively low melt temperature, printability (compatibility with currently commercially available printing inks), smooth surface finish, low noise, and a soft and pliable feel. In some examples, an intermediate layer may be formed of predominately HPDE, MDPE or LDPE, more preferably MDPE.

An intermediate layer formed of predominately MDPE may be particularly preferred with one or more skin layers formed predominately of LLDPE because it imparts the intermediate layer with a good combination of relatively higher melt temperature, co-extrusion compatibility with the skin layer(s), pliability, toughness and tensile strength.

In alternative examples, an intermediate layer may be formed partially or predominately of a thermoplastic polymer other than polyethylene, such as any of the polymers identified above, or any polymers identified as suitable for intermediate layers in, for example, U.S. Pat. Nos. 9,169,366 and 5,261,899; and U.S. Pat. Apps. Pub. Nos. 2015/03433748; 2015/0104627; and 2012/0237746, including bio-polymers or polymers having bio-based content as described in the latter three publications, such as, but not limited to, polylactic acid and thermoplastic starch. Additionally, an intermediate layer may include recycled thermoplastic polymer of any of the above-described types.

For purposes of balancing economy of polymer usage and maximization of tensile strength of the film, it may be desired that the total caliper of the film fall within a range of from 40 μm to 100 μm, more preferably from 50 μm to 90 μm, and even more preferably from 60 μm to 80 μm. For purposes of balancing economy of polymer usage, tensile strength and weldability, it may be desired that a three-layer film as described herein have a first and second skin layers each constituting from 15 percent to 35 percent of the weight of the film, and an intermediate layer constituting from 30 percent to 70 percent of the weight of the film.

Tie Layers

A multi-layer film as contemplated herein may comprise one or more tie layers disposed between other layers. A tie layer may be necessary when the polymers of adjoining layers would not otherwise be miscible or compatible so as to bond to each other during extrusion. For example, a tie layer between a polyethylene skin layer and an intermediate layer having a large polylactic acid content may be deemed desirable. Thus, for example, in a multilayer film having three main layers—two skin layers and an intermediate layer disposed between them, tie layers may be disposed between the intermediate layer and each of the skin layers. A tie layer may include one or more functionalized polyolefins. In some example, a tie layer may include from 5%, 10%, 20%, 30%, 40% or 45% to 55%, 60%, 70%, 80%, 90%, or 100%, by weight of the tie layer, of the one or more functionalized polyolefins. A tie layer may consist essentially of the one or more functionalized polyolefins.

For example, because of the significant difference in polarity between polylactic acid (PLA) and polyolefins, blends of these components typically result in incompatible systems with poor physical properties. A multilayer film having predominately polyethylene skin layers sandwiching an intermediate layer including PLA may also include one or more tie layers between the skin layers and the intermediate layer. This particular multi-layer structure may provide the MD and/or CD tensile properties useful for products currently made from polyethylene while incorporating a renewable feedstock (PLA). This arrangement may also enable downgauging (i.e., caliper reduction or basis weight reduction) of the film resulting from improvements in stiffness that can be used to drive sustainability and/or used as a cost savings.

The tie layer may comprise a functionalized polyolefin that possesses a polar component provided by one or more functional groups that is compatible with the PLA of the intermediate layer(s) and a non-polar component provided by an olefin that is compatible with one or more polyolefins of the adjacent skin layer. The polar component may, for example, be provided by one or more functional groups and the non-polar component may be provided by an olefin. The olefin component may generally be formed from any linear or branched α-olefin monomer, oligomer, or polymer (including copolymers) derived from an olefin monomer. The α-olefin monomer typically has from 2 to 14 carbon atoms and preferably from 2 to 6 carbon atoms. Examples of suitable monomers include, but not limited to, ethylene, propylene, butene, pentene, hexene, 2-methyl-1-propene, 3-methyl-1-pentene, 4-methyl-1-pentene, and 5-methyl-1-hexene. Examples of polyolefins include both homopolymers and copolymers, i.e., polyethylene, ethylene copolymers such as EPDM, polypropylene, propylene copolymers, and polymethylpentene polymers.

An olefin copolymer can include a minor amount of non-olefinic monomers, such as styrene, vinyl acetate, diene, or acrylic and non-acrylic monomer. Functional groups may be incorporated into the polymer backbone using a variety of known techniques. For example, a monomer containing the functional group may be grafted onto a polyolefin backbone to form a graft copolymer. Such grafting techniques are well known in the art and described, for instance, in U.S. Pat. No. 5,179,164. In other embodiments, the monomer containing the functional groups may be copolymerized with an olefin monomer to form a block or random copolymer. Regardless of the manner in which it is incorporated, the functional group of the compatibilizer may be any group that provides a polar segment to the molecule, such as a carboxyl group, acid anhydride group, acid amide group, imide group, carboxylate group, epoxy group, amino group, isocyanate group, group having oxazoline ring, hydroxyl group, and so forth. Maleic anhydride modified polyolefins are particularly suitable for use in the present invention. Such modified polyolefins are typically formed by grafting maleic anhydride onto a polymeric backbone material. Such maleated polyolefins are available from E. I. du Pont de Nemours and Company under the designation Fusabond, such as the P Series (chemically modified polypropylene), E Series (chemically modified polyethylene), C Series (chemically modified ethylene vinyl acetate), A Series (chemically modified ethylene acrylate copolymers or terpolymers), or N Series (chemically modified ethylene-propylene, ethylene-propylene diene monomer ("EPDM") or ethylene-octene). Alternatively, maleated polyolefins are also available from Chemtura Corp. under the designation POLYBOND and Eastman Chemical Company under the designation Eastman G SERIES, and AMPLIFY™ GR Functional Polymers (maleic anhydride grafted polyolefins). Other examples include LOTADER AX8900 (polyethylene-methyl acrylate-glycidyl methacrylate terpolymer) and LOTADER TX 8030 (polyethylene-acrylic ester-maleic anhydride terpolymer) available from Arkema, Columbes, France.

In some aspects, the tie layer can be a resin composition as disclosed in U.S. Pat. No. 8,114,522. This resin composition includes a modified PO resin and a terpene resin. Alternatively, it includes a polylactic acid resin, a modified polyolefin resin, and a hydrogenated petroleum resin. These compositions are suitable for use as a tie layer between the outer layer and the core layer.

In some examples, an outer layer and tie layer may be essentially combined as an outer layer by incorporating a functionalized polyolefin into one or both of the outer layers. In these instances, the multi-layer film may comprise 3 or 4 layers. In the case of a 3 layer film, the film may comprise a first outer layer comprising a polyolefin and/or a functionalized polyolefin, one or more core layers, and a second outer layer comprising a polyolefin and/or a functionalized polyolefin). In the case of a 4 layer film, the film may comprise a first outer layer comprising a polyolefin and/or a functionalized polyolefin, one or more core layers, a tie layer, and a second outer layer comprising a polyolefin.

Additives

Any of the layers of the multi-layer film may comprise small amounts of one or more additives. Typically, the additives may comprise less than about 10%, 5%, 4%, 3%, 2%, 1%, 0.5%, 0.1% or 0.01% by weight of the layer of the additive. Some non-limiting examples of classes of additives contemplated include perfumes, dyes, pigments, nanoparticles, antistatic agents, fillers, and combinations thereof. The layers disclosed herein can contain a single additive or a mixture of additives. For example, both a perfume and a colorant (e.g., pigment and/or dye) can be present.

A pigment or dye can be inorganic, organic, or a combination thereof. Specific examples of pigments and dyes contemplated include pigment Yellow (C.I. 14), pigment Red (C.I. 48:3), pigment Blue (C.I. 15:4), pigment Black (C.I. 7), and combinations thereof. Specific contemplated dyes include water soluble ink colorants like direct dyes, acid dyes, base dyes, and various solvent soluble dyes. Examples include, but are not limited to, FD&C Blue 1 (C.I. 42090:2), D&C Red 6 (C.I. 15850), D&C Red 7 (C.I. 15850:1), D&C Red 9 (C.I. 15585:1), D&C Red 21 (C.I. 45380:2), D&C Red 22 (C.I. 45380:3), D&C Red 27 (C.I. 45410:1), D&C Red 28 (C.I. 45410:2), D&C Red 30 (C.I. 73360), D&C Red 33 (C.I. 17200), D&C Red 34 (C.I. 15880:1), and FD&C Yellow 5 (C.I. 19140:1), FD&C Yellow 6 (C.I. 15985:1), FD&C Yellow 10 (C.I. 47005:1), D&C Orange 5 (C.I. 45370:2), and combinations thereof.

Contemplated fillers include, but are not limited to, inorganic fillers such as, for example, the oxides of magnesium, aluminum, silicon, and titanium. These materials can be added as inexpensive fillers or processing aides. Other inorganic materials that can function as fillers include hydrous magnesium silicate, titanium dioxide, calcium carbonate, clay, chalk, boron nitride, limestone, diatomaceous earth, mica glass quartz, and ceramics. Additionally, inorganic salts, including alkali metal salts, alkaline earth metal salts, phosphate salts, can be used. Additionally, alkyd resins can also be added to the composition. Alkyd resins can comprise a polyol, a polyacid or anhydride, and/or a fatty acid.

Additional contemplated additives include nucleating and clarifying agents for the thermoplastic polymer. Specific examples, suitable for polypropylene, for example, are benzoic acid and derivatives (e.g., sodium benzoate and lithium benzoate), as well as kaolin, talc and zinc glycerolate. Dibenzlidene sorbitol (DBS) is an example of a clarifying agent that can be used. Other nucleating agents that can be used are organocarboxylic acid salts, sodium phosphate and metal salts (e.g., aluminum dibenzoate). In one aspect, the nucleating or clarifying agents can be added in the range from 20 parts per million (20 ppm) to 20,000 ppm, or from 200 ppm to 2000 ppm, or from 1000 ppm to 1500 ppm. The addition of the nucleating agent can be used to improve the tensile and impact properties of the finished composition.

Additional contemplated additives include slip agents for purposes of reducing the coefficient of friction on one or both of the two outside surfaces of the film, or as anti-blocking agents. Suitable additives for this purpose may include but are not limited to fatty amides, for example, erucamide.

Additives may also include antioxidants such as BHT, and IRGANOX products, for example, IRGANOX 1076 and IRGANOX 1010. IRGANOX products are available from BASF Corporation, Florham Park, N.J., USA. Antioxidants may help reduce degradation of the film through oxidation, particularly during processing.

Contemplated surfactants include anionic surfactants, amphoteric surfactants, or a combination of anionic and amphoteric surfactants, and combinations thereof, such as surfactants disclosed, for example, in U.S. Pat. Nos. 3,929,678 and 4,259,217, and in EP 414 549, WO93/08876, and WO93/08874.

Contemplated nanoparticles include metals, metal oxides, allotropes of carbon, clays, organically modified clays, sulfates, nitrides, hydroxides, oxy/hydroxides, particulate water-insoluble polymers, silicates, phosphates and carbonates. Examples include silicon dioxide, carbon black, graphite, grapheme, fullerenes, expanded graphite, carbon nanotubes, talc, calcium carbonate, bentonite, montmorillonite, kaolin, zinc glycerolate, silica, aluminosilicates, boron nitride, aluminum nitride, barium sulfate, calcium sulfate, antimony oxide, feldspar, mica, nickel, copper, iron, cobalt, steel, gold, silver, platinum, aluminum, wollastonite, aluminum oxide, zirconium oxide, titanium dioxide, cerium oxide, zinc oxide, magnesium oxide, tin oxide, iron oxides (Fe203, Fe304) and mixtures thereof. Nanoparticles can increase strength, thermal stability, and/or abrasion resistance of the compositions disclosed herein, and can give the compositions electric properties.

Contemplated anti-static agents include fabric softeners that are known to provide antistatic benefits. These can include those fabric softeners having a fatty acyl group that has an iodine value of greater than 20, such as N,N-di(tallowoyl-oxy-ethyl)-N,N-dimethyl ammonium methylsulfate.

In particular aspects, the filler can comprise renewable fillers. These can include, but are not limited to, lipids (e.g., hydrogenated soybean oil, hydrogenated castor oil), cellulosics (e.g., cotton, wood, hemp, paperboard), lignin, bamboo, straw, grass, kenaf, cellulosic fiber, chitin, chitosan, flax, keratin, algae fillers, natural rubber, nanocrystalline starch, nanocrystalline cellulose, collagen, whey, gluten, and combinations thereof.

Particular combinations of film layers, film layer compositions and pigment additives for maximizing package film opacity while providing a film that effectively balances weldability, tensile strength and cost effectiveness are described in PCT Application No. CN2016/088098, the disclosure of which is incorporated herein by reference.

Opening Features

Figure 6:
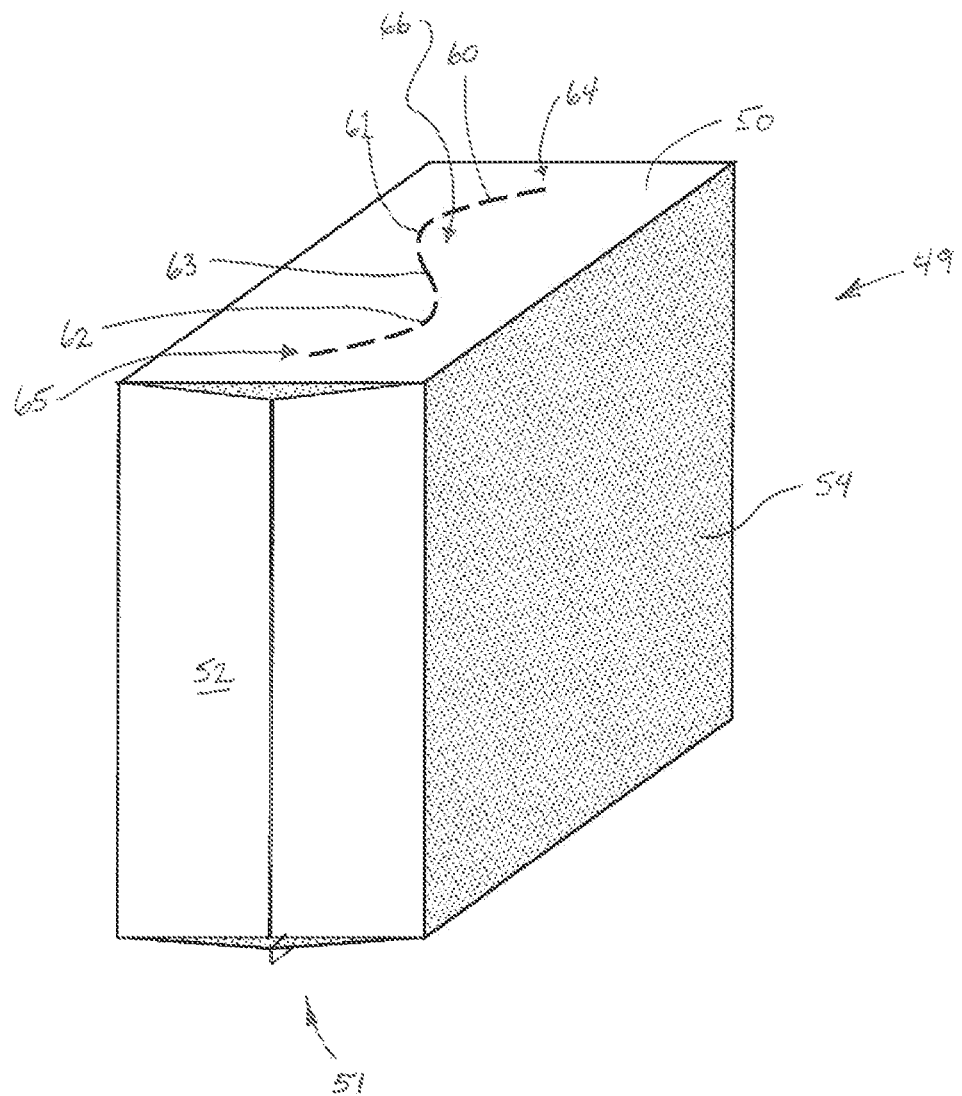
FIG. 6 is a perspective view of a film package that may be used to contain a stack of diapers such as the stack shown in FIGS. 4A and 4B, depicting a configuration of a path of perforations or scoring, in one example.
Figure 7:
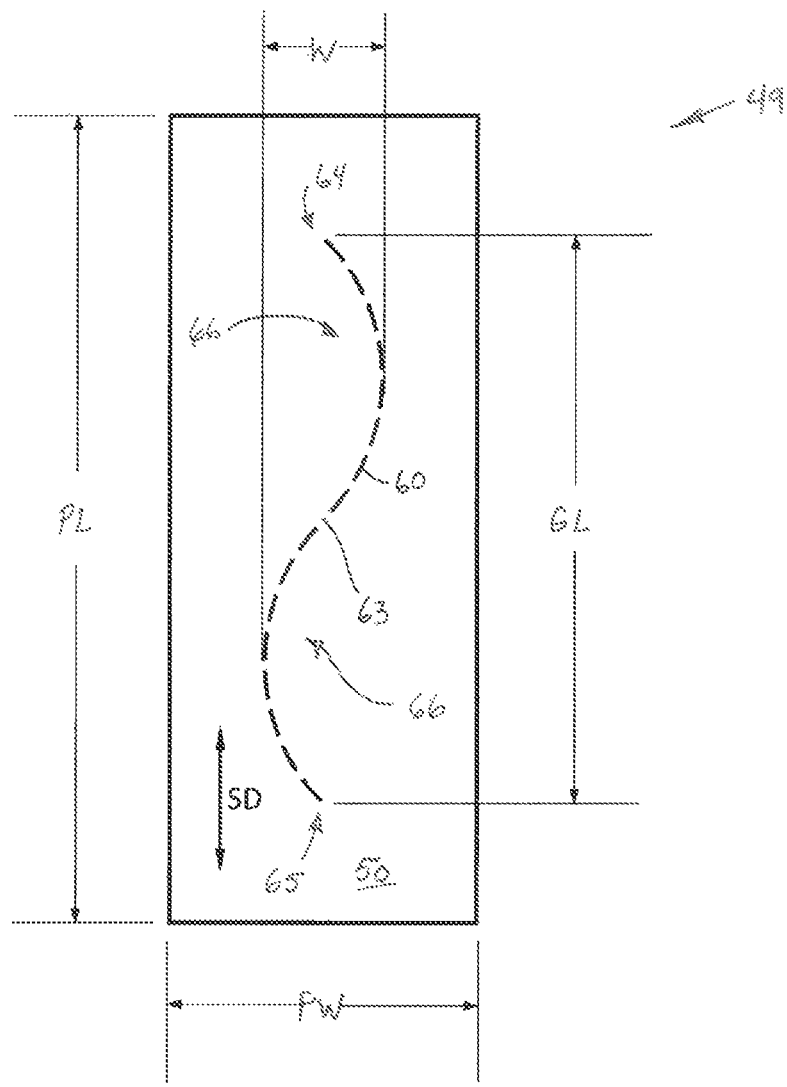
FIG. 7 is a view of a surface of a film package adjacent one of first or second sides of a stack of articles contained therein, depicting a configuration of a path of perforations or scoring, in one example.
Figure 8:
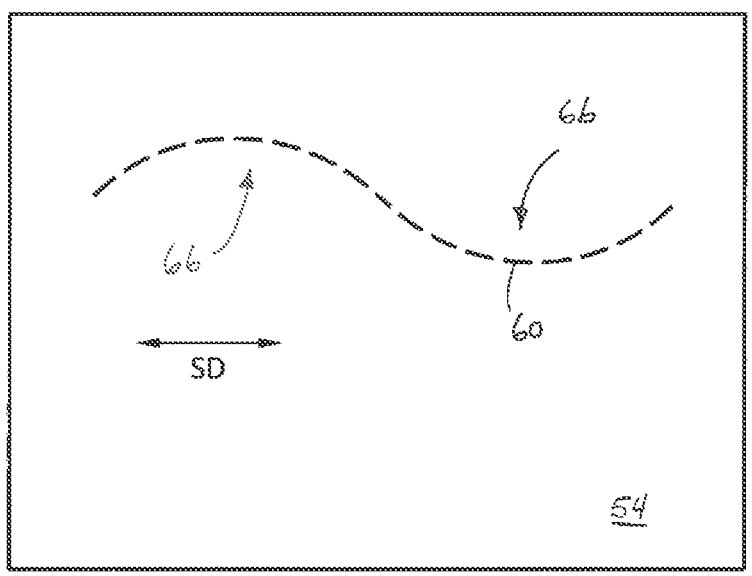
FIG. 8 is a view of a surface of a film package adjacent one of fifth or sixth sides of a stack of articles contained therein, depicting a configuration of a path of perforations or scoring, in another example.
Figure 9:
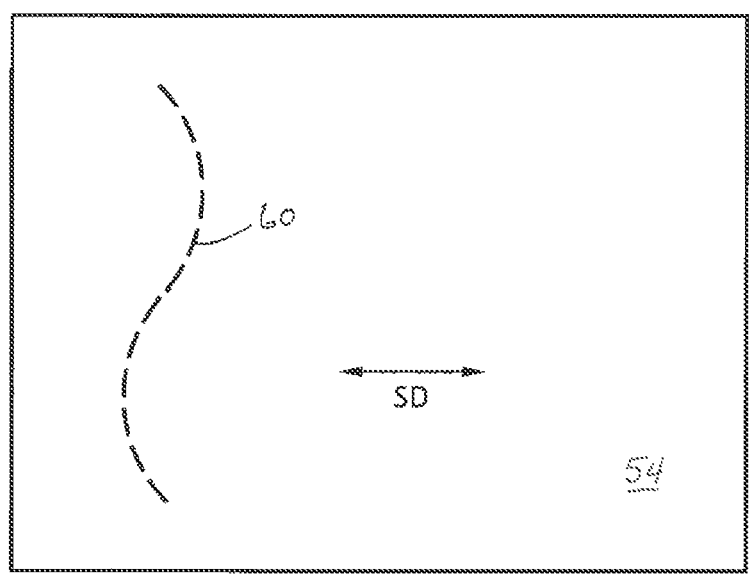
FIG. 9 is a view of a surface of a film package adjacent one of fifth or sixth sides of a stack of articles contained therein, depicting a configuration of a path of perforations or scoring, in another example.

Referring to FIGS. 6 and 7, a film package containing a stack of disposable absorbent articles such as disposable diapers, training pants or adult incontinence pants, may be imparted with features that facilitate opening without unwanted deformation or destruction of the package, so that the opened packaged may be used, following opening, as a container to store the supply of unused product.

In the examples depicted in FIGS. 6 and 7, the package may be provided with a path 60 of perforations or scoring in the film. The path 60 may be continuous. (For purposes herein, a "continuous" path of perforations or scoring is a singular path of individual, successive, mechanically-created partial or complete perforations, a singular path of individual, successive laser-scored partial or complete perforations, or a continuous, singular path of laser scoring, that is uninterrupted by an unperforated/unscored portion of the film of a length between successive perforations or scoring greater than 8 mm.)

Figure 16:
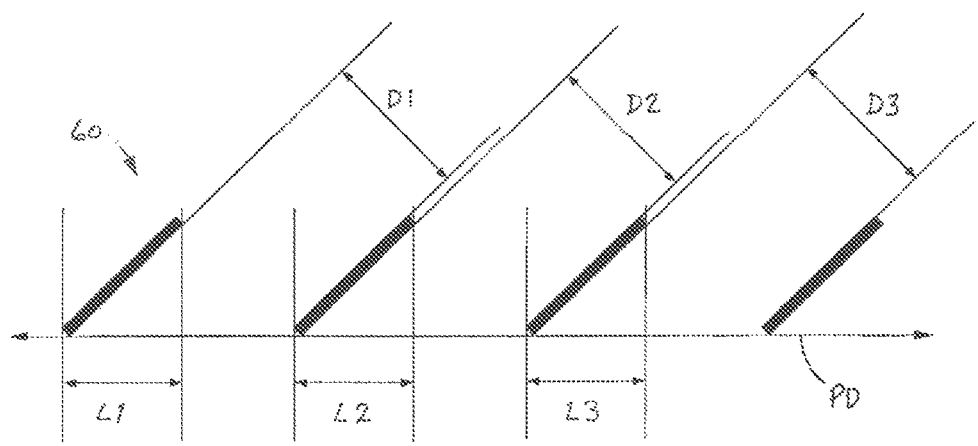
FIG. 16 is a schematic plan view depiction of an example of a configuration of perforations, illustrating measurements for determining cut-to-land ratio.

Individual perforations defining a path 60 may have any configuration suitable for propagating a tear in the package film along the path. Non-limiting examples are depicted in FIGS. 15A-15D. Where the path 60 of perforations comprises a plurality of individual mechanically-created perforations or individual laser-scored perforations, it may be desired that the path have a cut-to-land ratio of at least 0.67:1 and no greater than 3:1. For film packages of the type contemplated herein, it is believed that a cut-to-land ratio within this range strikes a suitable balance between providing for ease of package opening and minimized strain deformation of the film along the path during opening, and avoiding premature, unintended package bursting or opening, and retaining structural integrity of the package during shipping, handling and other events prior to retail purchase and intentional opening by the consumer. (For purposes herein, the "cut-to-land ratio" of a path of perforations is the ratio of the aggregate of the lengths of the perforations extending along the path direction, to the aggregate of the minimum distances of unperforated/unscored portions of the film between successive perforations. Referring to FIG. 16, for example, in which a portion of a path of successive diagonally-tilted rectangular perforations is depicted lying along path direction PD, the cut-to-land ratio is (L1+L2+L3):(D1+D2+D3).

In another example, a path of scoring may comprise a single, uninterrupted line of laser scoring that does not entirely penetrate the film but is configured to promote neat tear propagation along the path, such as described in U.S. Application Pub. No. 2015/0266663, the disclosure of which is incorporated herein by reference.

For both ease of opening and simplification of manufacturing, it may be preferred that the path 60 of perforations or scoring defining the package opening does not traverse a gusset (such as gussets 52b and 53b), because a gusset structure includes more than one layer of package film (e.g., three layers), making propagation of a neat tear along the path more difficult.

Figure 13A:
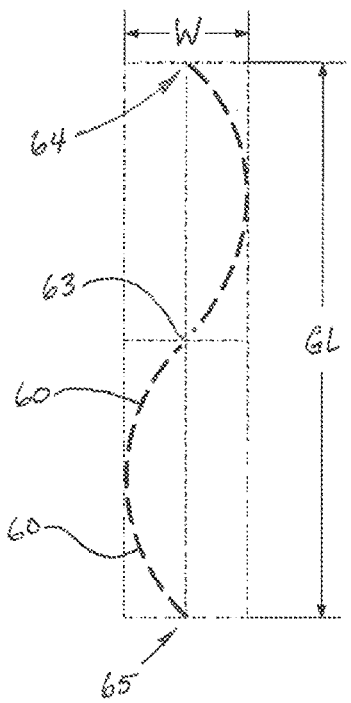
FIGS. 13A, 13B and 14 are views of three examples of paths of perforations or scoring, illustrating particular measurements of dimensions.
Figure 13B:
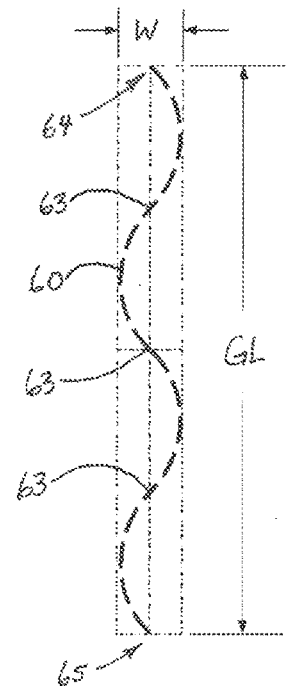
Figure 14:
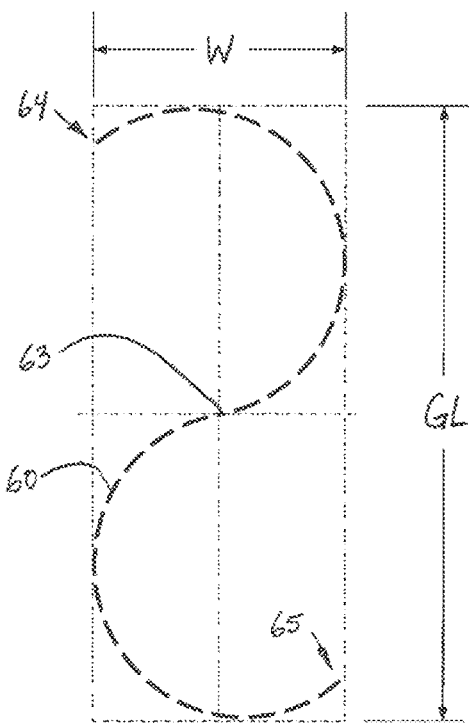
Figure 15A:
FIGS. 15A-15D are schematic plan view depictions of examples of configurations of perforations.
Figure 15B:
Figure 15C:
Figure 15D:

As may be appreciated from FIGS. 6 and 7, a path 60 of perforations or scoring may be configured to define a serpentine-shape, defined entirely on, or confined to, one of the six surfaces of the package, having a first curve 61, a second curve 62 and an inflection point 63 therebetween. This will facilitate a corresponding serpentine-shaped tear in the package film and a serpentine-shaped access opening into the package along that surface. It has been discovered that a tear and opening having such a configuration provide several benefits. A serpentine-shaped path 60 may define a single set of two curved sections that are oppositely-oriented and joined at an inflection point 63, as suggested in FIGS. 6-10 and 13A. In other examples, however, a serpentine-shaped path 60 may include more than two curved sections, or more than one set of oppositely-oriented curved sections, each being joined to the next, with a plurality of inflection points 63, as suggested in FIG. 13B.

When serpentine-shaped path 60 is a simple, relatively narrow and singular path along one package surface, the resulting tear along the path may allow the package to retain a substantial portion of its structural integrity, and thereby retain its suitability for storing the unused supply of articles within, following package opening.

Differing from a straight-line tear path, however, the serpentine-shaped tear path, combined with the flexibility and pliability of the film, provides an opening with flap structures 66 (as identified in FIGS. 6-8) defined by the curves in the path, that provide substantial width of access to the stack within, along a direction transverse to the tear opening length GL. This makes withdrawal of articles from a stack easier, particularly immediately following opening, when the stack is most compressed.

Differing from a single-curve opening tear, when the serpentine-shape is imparted with one or more features as described herein, the flap structures 66 resulting from a serpentine-shaped tear configuration tend to be pulled to a closed position, i.e., tend to return to their pre-opening positions and lay flat against the adjacent side of the stack 40 within, as a result of the geometry of the serpentine-shape and tension in the package film. Thus, the flaps help block entry of airborne dust or other contaminants into the package following opening, helping to protect the unused supply of articles from contamination.

To promote the above-described behavior of the opening and flap structures 66, one or more of several additional features may be provided in conjunction with a generally serpentine-shaped path 60 of perforations or scoring.

The greatest length GL of the serpentine-shape of the path 60 may be oriented along any direction, e.g., along the stacking direction (FIG. 8), transverse to the stacking direction (FIG. 9), or along any other direction. Referring to FIGS. 7, 8, 13A, 13B and 14, however, it may be desired that the greatest length GL of the path 60 be approximately parallel to the stack direction SD of the stack within the package, or is at least substantially aligned therewith. Herein, "substantially aligned" means that a line along which the greatest length GL may be measured forms an angle with the stack direction, in the plane of the package surface on which the path is present, of less than 45 degrees, more preferably less than 30 degrees, and even more preferably less than 15 degrees, and most preferably approximately zero. (The greatest length GL of a serpentine-shaped path 60 is the length (longer dimension) of the rectangle that can be identified, that entirely but most closely circumscribes the path 60. Correspondingly, the width W of the path 60 is the width of such circumscribing rectangle. See, e.g., FIGS. 13A, 13B and 14.) When the greatest length GL of the path 60 is aligned with the stack direction SD as described, tension in the package film resulting from stack compression tends to pull flap structures 66 to a closed position, following package opening. Further, when the greatest length GL of the serpentine-shaped path 60 is substantially aligned with the stack direction SD, compressive forces within the package and resulting tension in the film along the stack direction SD are less transverse to the path 60, and thereby less likely to cause premature rupturing or tearing of the package at the path 60, e.g., during shipping and handling prior to purchase by the consumer. Further, referring to FIG. 7, in order to provide the consumer with maximized access to the stack 40, while substantially preserving the structure of the package for storage of the unused supply of article therein, it may be desired that the greatest length GL of the path 60 of perforations be from 50 to 90 percent of the package length PL, along the stacking direction.

It may be desired that the aspect ratio of greatest length GL to width W (GL/W) of the path 60 be at least 3.5, more preferably at least 5, even more preferably at least 7, and still more preferably at least 10. A limited aspect ratio, combined with film tension as described above, strikes a good balance between providing a suitable opening access width, while limiting the width of the flap structures 66 relating the greatest length GL, helping to ensure that they tend to close following package opening. Further toward this purposes, it may be desired that the path 60 have substantial rotational symmetry of order 2, about inflection point(s) 63. As reflected in FIG. 14, the serpentine-shape defined by the path 60 may have one or two slight return portions adjacent path endpoints 64, 65, such that, for example, the distance between endpoints 64, 65 is less than greatest length GL. It may be preferred, however, that the distance between endpoints 65, 65 be substantially the same as greatest length GL, which reflects the absence of any return portions. This feature helps further ensure that the flap structures 66 will tend to return to a closed position following opening, rather than being overly floppy and prone to laying in an open position.

Serpentine-shaped path 60 of perforations or scoring may be located on any of the six package surfaces. It may be desired, however, that it be located on one of the four faces of the package adjacent first side 41, second side 42, third side 43 or fourth side 44 of stack 40. This provides the consumer with immediate visual and/or tactile access to one of the sides of the stack defined by either side edges or end edges of a plurality of the articles in the stack, for easier insertion of fingers between adjacent articles, grasping of a single article or group of articles, and withdrawal from the stack through the opening. Further toward this purpose it may be desired that the path 60 be located on the package surface adjacent first side 41 of the stack 40, to provide immediate visual and/or tactile access to the fold noses 30, providing for easiest tactile identification and grasping of individual ones of articles in the stack, for withdrawal through the opening.

Figure 5D:
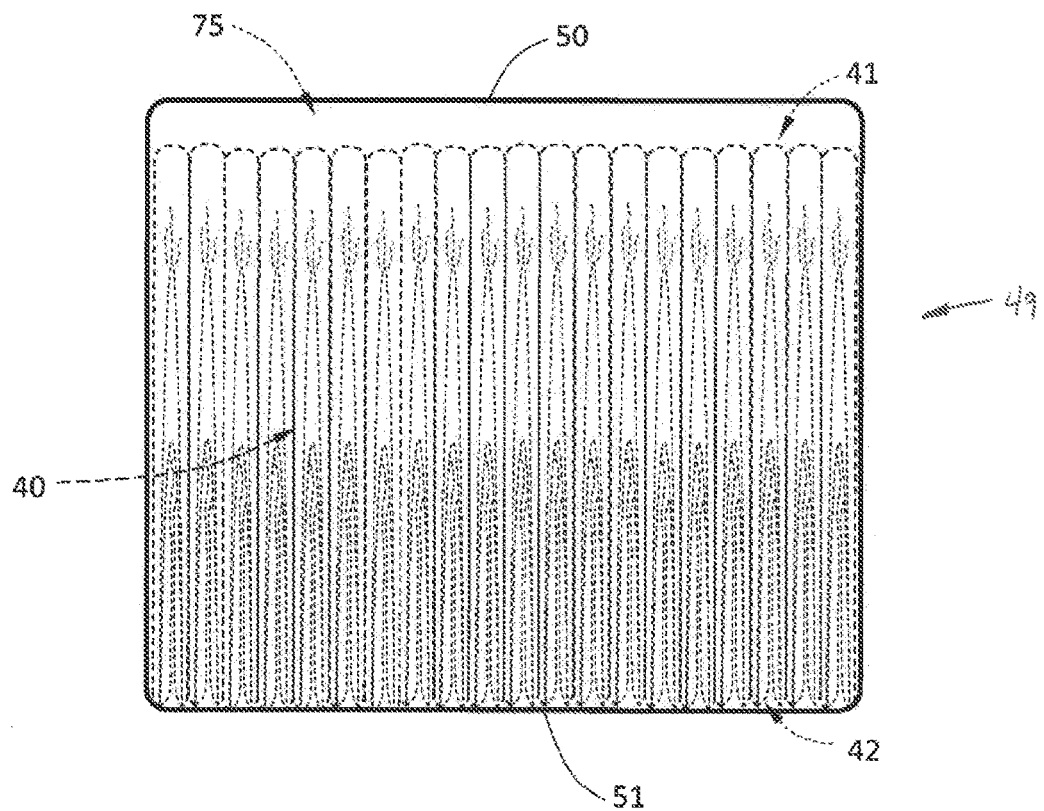
FIG. 5D is a side view of a film package depicted with a stack of folded articles within.

In some examples it may be preferred that the package include some head space therewithin. This is illustrated in FIG. 5D, depicting head space 75 within the package above side 41 of stack 40. This results in some slack film material package structure on at least one side of the stack prior to package opening. This extra material provided, for example, along the direction of the package height, may give the consumer extra material to conveniently grasp when, for example, tearing along an path of perforations or scoring in the package film adjacent the head space, to create an access opening in the package.

Figure 10:
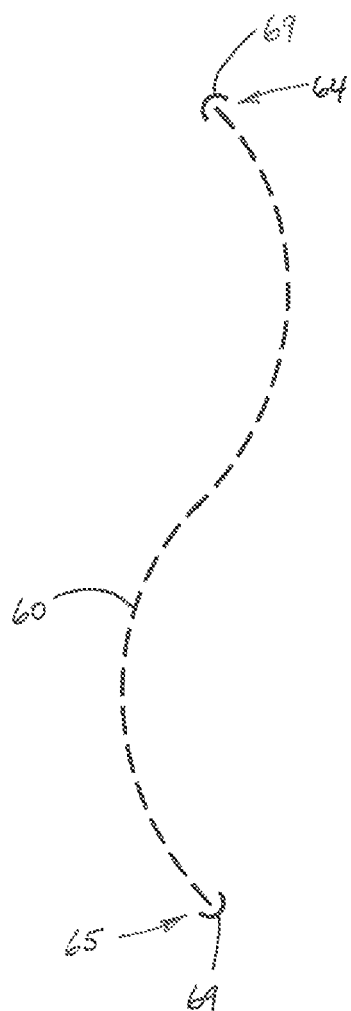
FIG. 10 is a view of a path of perforations or scoring, having tearing stress dispersion features, in one example.

Referring to FIG. 10, in order to reduce chances that a consumer opening the package will tear the package film past endpoints 64, 65 of the path 60 of perforations or scoring, and deform the package film and/or reduce the utility of the flap structures 66, it may be desired to include a tactilely perceivable tearing stress dispersion feature 69 proximate one or both endpoints 64, 65. In the example depicted in FIG. 10, tearing stress dispersion feature 69 is a semi-circular perforation or cut running transverse to the direction of the path 60, which serves to disperse tearing stresses concentrated at the endpoint, and thereby obstruct tear propagation in a way that may be perceived tactilely by the consumer they are opening the package. It will be appreciated that tearing stress dispersion feature 69 may have other forms including other shapes of cuts or perforations through the film that extend transversely to the direction of the path 60, added reinforcing strips, tapes, etc.

Through experimentation and observation of consumer behavior it is believed that consumers prefer to have most immediate access to a side of the stack 40 at which the single fold noses 30 of the diapers are present, i.e., first side 41. This may be because consumers find it easiest to quickly identify, grasp and withdraw a single product item from the stack by the tactile feel of the single fold noses. Conversely, the plurality of side and waist edges of a single folded diaper in a stack are typically less distinguishable by touch, from those of neighboring diapers in the stack. This preference may indicate a further preference that all fold noses of the stack be present at only one side the stack, i.e., only one of sides 41, 42. For easiest consumer access to the fold noses, it may be desired that the path 60 of perforations or scoring defining the serpentine-shaped opening, be disposed generally closer to one of the package surfaces, e.g., one of surfaces 50, 51, that is adjacent the single fold noses of the diapers in the stack 40, thereby locating flap structures 66 proximate first side 41 of stack 40—and preferably the surface most proximate the fold noses.

When it is defined by fold noses 30, the first side 41 of a stack 40 is often more flat and firm, than the opposing second side 42. For marketing purposes it may be preferred to design the package with the expectation that one of the larger surfaces 54, 55 will face outward (i.e., face the aisle) when the package is on the shelf in a retail store. This provides for consumer view of one of the larger surfaces, with more surface area available that can be imprinted with commercial artwork, graphics and product information. Thus, the package and stack may be configured such that the first side 41 of the stack 40 with the fold noses is located at, and forms the shape of, the "bottom" of the package as it is shelved, and the sides of the stack with the side edges 34, 35 of the diapers will be respective adjacent the larger surfaces 54, 55, which will be substantially vertical when the package rests on its "bottom." The firmer, flatter first side 41 of the stack 40 provides for a firmer, flatter package "bottom," that enhances the ability of the package to rest stably on the shelf, and be less prone to leaning and/or tipping over. Thus, it may desired to locate the path 60 of perforations or scoring, defining a serpentine-shaped opening and corresponding flap structures 66, nearer or on the "bottom" of the package, so as to define the opening proximate the first side of the stack. Visible verbal and graphic information on sides 54 and 55 may be arranged so as to appear upright and legible with the package resting with the first side of the stack at the bottom.

This configuration, however, may be counterintuitive to consumers, who may ordinarily expect to open a package at what they perceive to be its "top." Accordingly, it may be desired to provide one or more indicia on the package that visibly, tactilely and/or verbally identify the location of the path 60 of perforations or scoring. The one or more indicia may include, but are not limited to, an imprinted path marking or tracing path 60, of a color that visibly contrasts with surrounding package printing; tactilely perceivable indicia; verbal indicia; other graphic indicia or any combination thereof. In one example, the indicia may include embossing or other surface texturing of the film, configured to provide raised, tactilely perceivable features that suggest the presence of the path 60 of perforations or scoring for opening. In a particular example, embossing may be configured to suggest one or more ridges following lines or paths proximate and parallel to path 60. In another particular example, embossing may be configured to suggest one or more lines or paths of stitches following paths proximate and parallel to path 60. Additionally, the package may include verbal or graphic indicia that instruct or encourage the consumer to flip the package over, putting the perceived "top" side down and "bottom" side up, for opening and/or storage. Additionally, or alternatively, commercial artwork, graphics, and verbal information printed onto the film of the package may be configured in some examples to have an upright appearance regardless of which surface 50, 51 of the package is disposed at the top as the package is placed on a horizontal surface. In some examples, the printed material may be configured to suggest that either of surfaces 50, 51 can appropriately be deemed the "top" of the package.

Figure 11:
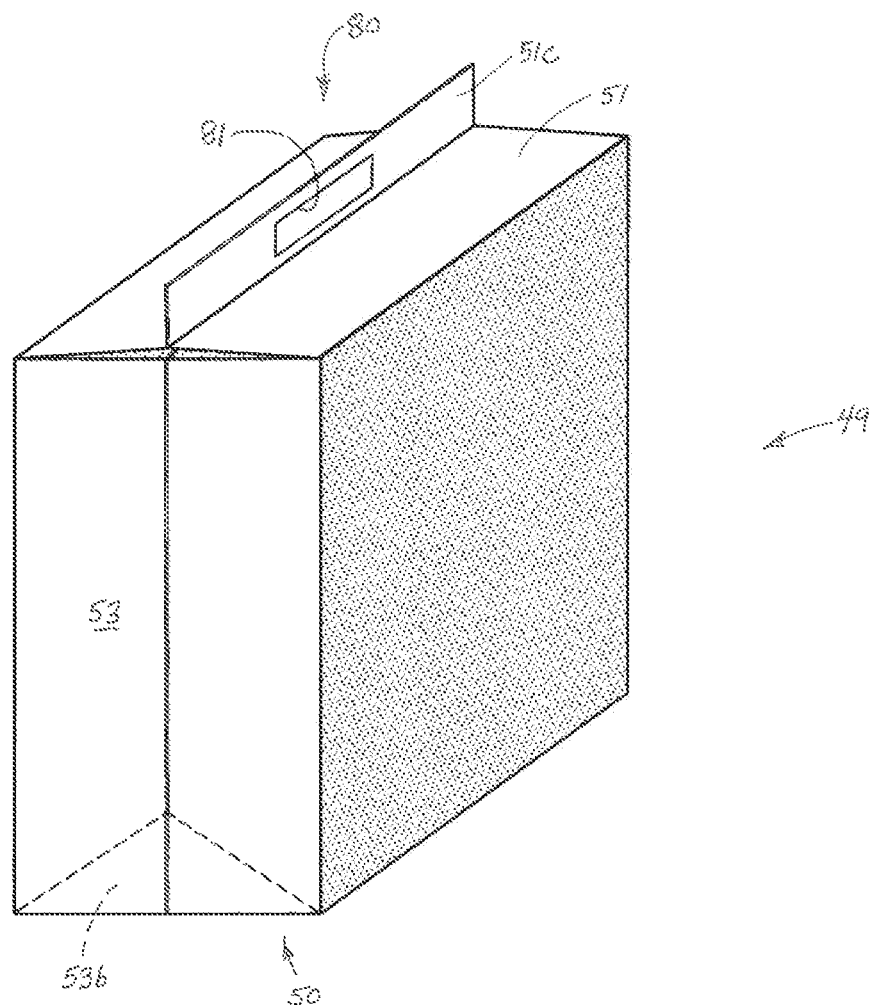
FIG. 11 is a perspective of a film package that may be used to contain a stack of disposable absorbent articles such as the stack shown in FIG. 4, having a handle, in one example.
Figure 12:
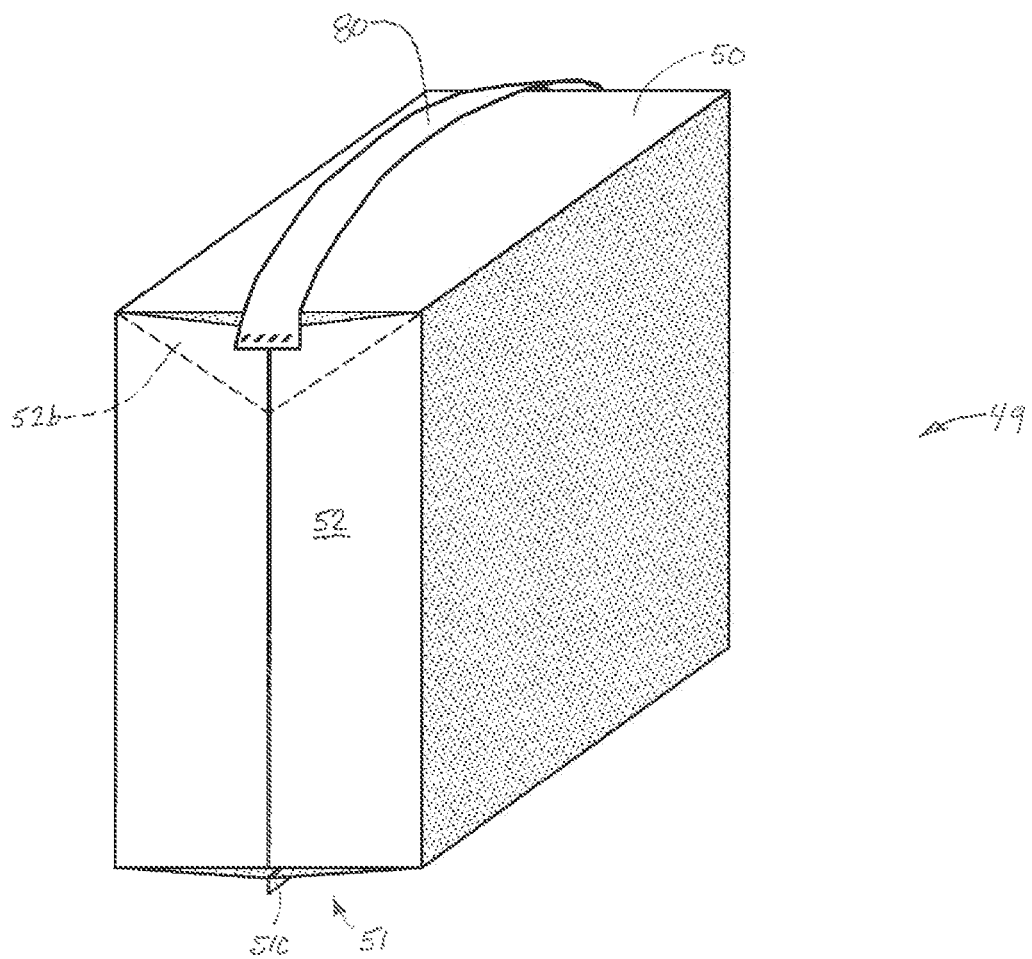
FIG. 12 is a perspective of a film package that may be used to contain a stack of disposable absorbent articles such as the stack shown in FIG. 4, having a handle, in another example.

Referring to FIGS. 11 and 12, particularly for a larger package 49, it may be desired that the package include a carrying handle 80. In one example depicted in FIG. 11, a carrying handle 80 may be formed of an extension of a fin 51*c* extending from the package from an end seam 51. The end seam fin 51*c* may have a handle cutout 81 made therethrough, providing a carrying handle 80. In another example depicted in FIG. 12, a carrying handle 80 may be formed of a strip of polymer film. In a more particular example, the strip may have its long dimension oriented along the stack direction SD. The strip may be bonded by any suitable mechanism to portions of the package or package film. Where a handle 80 is included, it may be desired that the path 60 of perforations or scoring be located on a package surface other than the surface adjacent the handle, so that the handle structure does not interfere with creation of an opening, or interfere with access to the contents. In other examples, however, it may be desired that path 60 be located on the surface adjacent the handle (in FIGS. 11 and 12, on surface 51 or 50, respectively). In such alternative examples, the handle structure (or a fin in which a handle may be formed) may be deemed useful for retaining greater structural integrity for the areas of the package adjacent the flap structures.

The following non-limiting examples are contemplated within the scope of the description herein:

1. A package formed of flexible polymeric film, containing a stack (40) of folded disposable absorbent articles (10), the stack (40) having an approximately rectangular cuboid shape and comprising:
   a plurality of the articles, similarly folded, each of the plurality of folded articles comprising two opposing faces lying along approximately parallel planes, and a fold with a fold nose (30);
      the plurality of the articles being arranged with one of the opposing faces of one in contact with one of the opposing faces of a next adjacent one, and wherein the fold noses of some or all of the plurality are disposed approximately along a first side (41) of the cuboid shaped stack (40);
      a second side (42) opposite to and approximately parallel with the first side (41); opposing third and fourth sides (43, 44) that are approximately parallel to each other and approximately perpendicular to the first and second sides; and opposing fifth and sixth sides (45, 46) that are approximately parallel to each other and approximately perpendicular to the fourth and fifth sides;
      a stacking direction approximately perpendicular to the parallel planes and to the fifth and sixth sides; and
      a stack length (SL) measured from a first outward-facing side (36) of a first article in the stack to an opposing second outward-facing side (37) of a last article in the stack, along the stacking direction;
   the flexible polymeric film enclosing and wrapping the stack and thereby approximately assuming the rectangular cuboid shape and forming the package, the package thereby having six outward-facing surfaces comprising:
      a first package surface (50) having no seam thereacross;
      a second package surface (51) opposite the first package surface, the second package surface having a seam (51*b*) extending thereacross;
      an opposing pair of third and fourth package surfaces (52, 53), the third and fourth package surfaces each having a seam extending therealong; and
      an opposing pair of fifth and sixth package surfaces (54, 55);
   the package having:
      a continuous single path (60) of perforations or scoring in the film beginning at a first endpoint (64) and ending at a second endpoint (65), the path defining a serpentine shape having a first curve (61) that is convex with respect to a reference point, an inflection point (63), and a second curve (62) that is concave with respect to the reference point, the serpentine shape being present substantially entirely on one of the six outward facing surfaces.

2. The package of example 1 wherein the serpentine shape has a greatest measurable length (GL) measured along a length direction and a width (W) measured along a width direction perpendicular to the length direction, the serpentine shape having an aspect ratio of greatest measurable length to width at least 3.5, more preferably at least 5, even more preferably at least 7, and still more preferably at least 10.

3. The package of either of the preceding examples wherein the greatest measurable length of the serpentine shape lies along a direction that is transverse to the stacking direction.

4. The package of either of examples 1 or 2 wherein the greatest measurable length of the serpentine shape lies along a direction that is substantially aligned with the stacking direction.

5. The package of any of the preceding examples wherein the serpentine shape is defined on one of the six outward facing surfaces having no seam thereacross.

6. The package of any of the preceding examples wherein the serpentine shape is defined on one of the six outward-facing surfaces adjacent the first side (41) of the stack (40).

7. The package of any of the preceding examples wherein the greatest measurable length (GL) of the serpentine shape is from 50 percent to 90 percent of the stack length (SL).

8. The package of any of the preceding examples wherein the greatest measurable length of the serpentine shape exists along a line connecting the first endpoint and the second endpoint.

9. The package of any of the preceding examples wherein the serpentine shape has substantial rotational symmetry of order 2, about the inflection point.

10. The package of any of the preceding examples wherein one or preferably both of the first and second endpoints comprises a tear stress dispersing feature.

11. The package of any of the preceding examples wherein the continuous single path comprises a path of perforations with a cut-to-land ratio of at least 0.67:1 and no greater than 3:1.

12. The package of any of the preceding examples wherein the continuous single path comprises a path of intermittent laser scoring.

13. The package of any of examples 1-10 wherein the continuous single path comprises a continuous path of laser scoring.
14. The package of any of the preceding examples wherein the perforations or scoring do not completely penetrate the film.
15. The package of any of the preceding examples wherein the film is a multilayer film.
16. The package of any of the preceding examples comprising a carrying handle (80) disposed adjacent one of the first package surface (50) and the second package surface (51).
17. The package of example 16 wherein the carrying handle (80) is disposed adjacent the second package surface (51).
18. The package of example 17 comprising an indicium comprising a verbal or graphically communicated instruction to identify the continuous single path and/or to flip the package over for opening.
19. The package of any of examples 16-18 wherein the carrying handle (80) comprises a strip of polymer film extending along the stacking direction.
20. The package of any of examples 16-18 having a seam fin (51c) extending from the second package surface (51), wherein the carrying handle is formed in the seam fin.

The dimensions and values disclosed herein are not to be understood as being strictly limited to the exact numerical values recited. Instead, unless otherwise specified, each such dimension is intended to mean both the recited value and a functionally equivalent range surrounding that value.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A package formed of flexible polymeric film, containing a stack of folded disposable absorbent articles,
the stack having an approximately rectangular cuboid shape and comprising:
a plurality of the articles, similarly folded, each of the plurality of folded articles comprising two opposing faces lying along approximately parallel planes, and a fold with a fold nose;
the plurality of the articles being arranged with one of the opposing faces of one in contact with one of the opposing faces of a next adjacent one, and wherein the fold noses of some or all of the plurality are disposed approximately along a first side of the cuboid shaped stack;
a second side opposite to and approximately parallel with the first side; opposing third and fourth sides that are approximately parallel to each other and approximately perpendicular to the first and second sides; and opposing fifth and sixth sides that are approximately parallel to each other and approximately perpendicular to the fourth and fifth sides;
a stacking direction approximately perpendicular to the parallel planes and to the fifth and sixth sides; and
a stack length measured from a first outward-facing side of a first article in the stack to an opposing second outward-facing side of a last article in the stack, along the stacking direction;
the flexible polymeric film enclosing and wrapping the stack and thereby approximately assuming the rectangular cuboid shape and forming the package, the package thereby having six outward-facing surfaces comprising:
a first package surface having no seam thereacross;
a second package surface opposite the first package surface, the second package surface having a seam extending thereacross;
an opposing pair of third and fourth package surfaces, the third and fourth package surfaces each having a seam extending therealong; and
an opposing pair of fifth and sixth package surfaces;
the package having:
a path of perforations or scoring in the film beginning at a first endpoint and ending at a second endpoint, the path defining a serpentine shape having a first curve that is convex with respect to a reference point, an inflection point, and a second curve that is concave with respect to the reference point, the serpentine shape being present substantially entirely on one of the six outward facing surfaces,
a pair of adjacent flap structures being defined by the path of perforations or scoring comprising a first flap comprising a first terminal end defined by the first curve and a second flap comprising a second terminal end defined by the second curve, wherein each of the first flap and the second flap extend more than 50% of the width of the one of the six outward facing surfaces.

2. The package of claim 1 wherein the serpentine shape has a greatest measurable length measured along a length direction and a width measured along a width direction perpendicular to the length direction, the serpentine shape having an aspect ratio of greatest measurable length to width at least 3.5.

3. The package of claim 1 wherein the serpentine shape is defined on one of the six outward facing surfaces having no seam thereacross.

4. The package of claim 1 wherein the serpentine shape is defined on one of the six outward-facing surfaces adjacent the first side of the stack.

5. The package of claim 1 wherein the serpentine shape has substantial rotational symmetry of order 2, about the inflection point.

6. The package of claim 1 wherein at least one of the first and second endpoints comprises a tear stress dispersing feature.

7. The package of claim 1 wherein the path comprises a path of perforations with a cut-to-land ratio of at least 0.67:1 and no greater than 3:1.

8. The package of claim 1 wherein the path comprises a path of intermittent laser scoring.

9. The package of claim 1 wherein the path comprises a continuous path of laser scoring.

10. The package of claim 1 wherein the perforations or scoring do not completely penetrate the film.

11. The package of claim 1 wherein the film is a multi-layer film.

* * * * *